United States Patent

Huang

[11] Patent Number: 5,973,267
[45] Date of Patent: Oct. 26, 1999

[54] PROBE SHEATH

[76] Inventor: Jason Huang, 4th Fl., No. 8, Lane 24, Ho-Ping Rd., Pan-Chiao City, Taipei Hsien, Taiwan

[21] Appl. No.: 09/114,047
[22] Filed: Jul. 13, 1998
[51] Int. Cl.⁶ .............................. H01B 7/18; H01R 13/02
[52] U.S. Cl. ....................... 174/102 R; 439/888
[58] Field of Search ................... 174/102 R, 102 C, 174/102 E, 74 A, 78, 267, 108; 439/888

[56] References Cited

U.S. PATENT DOCUMENTS

| 3,123,664 | 3/1964 | Logan ........................... 174/88 R |
| 3,880,282 | 4/1975 | Naumann ....................... 206/306 |
| 4,168,873 | 9/1979 | Luna ............................. 439/391 |
| 4,263,547 | 4/1981 | Johnson ........................ 324/72.5 |
| 4,341,992 | 7/1982 | Goldstein ..................... 324/65 R |
| 5,420,519 | 5/1995 | Stowers et al. ............... 324/754 |
| 5,646,370 | 7/1997 | Perkins ......................... 174/78 X |

Primary Examiner—Kristine Kincaid
Assistant Examiner—Chau N. Nguyen
Attorney, Agent, or Firm—Bacon & Thomas

[57] ABSTRACT

A metal probe sheath includes an end piece at one end of a tubular body thereof, a neck on the middle of the end piece to which the bare conductor of a lead wire is connected, a plurality of annular grooves around the neck to which the bare conductor of the lead wire is fastened, and two stop portions at two opposite ends of the neck to stop the lead wire in place.

4 Claims, 4 Drawing Sheets

PROBE SHEATH

BACKGROUND OF THE INVENTION

The present invention relates to a probe sheath for holding a probe, and more particularly to such a probe sheath which facilitates the installation of a lead wire, and keeps the installed lead wire firmly retained in place to provide good conductivity.

FIG. 1 shows a probe sheath for holding a probe according to the prior art. This structure of probe sheath comprises a tubular body, and a shaft. The tubular body has a flange raised around the periphery for positioning in a plug hole on an implement, and a reduced extension tube at one end. The shaft is fastened to the reduced extension tube to hold a lead wire. The lead wire has one end wound round the shaft. The tubular body of the probe sheath is made from a metal (copper tube) by drawing. The complicated drawing process greatly increases the manufacturing cost of the probe sheath. Furthermore, because the bare conductor of the lead wire is wound round the smooth outside wall of the shaft, the lead wire tends to be disconnected from the shaft.

SUMMARY OF THE INVENTION

It is one object of the present invention to provide a probe sheath which facilitates the installation of a lead wire, and keeps the installed lead wire firmly retained in place to provide good conductivity. It is another object of the present invention to provide a probe sheath which is easy and inexpensive to manufacture. According to one aspect of the present invention, the probe sheath is made by stamping a metal sheet into shape, and then rolling up the stamped metal sheet into a tubular member. According to another aspect of the present invention, the probe sheath comprises an end piece at on end of a tubular body thereof, a neck one the middle of the end piece to which the bare conductor of a lead wire is connected, a plurality of annular grooves around the neck to which the bare conductor of the lead wire is fastened, and two stop portions at two opposite ends of the neck to stop the lead wire in place.

DETAILED DESCRIPTION OF THE PREFERRED EMBODIMENT

Figure 1:
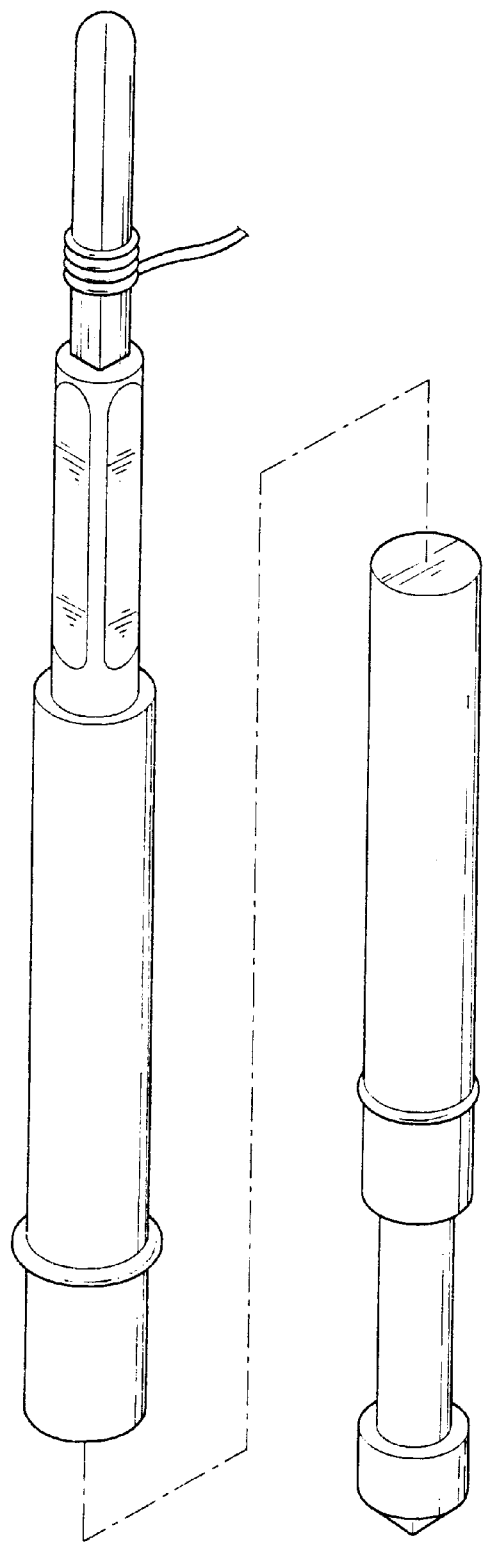
FIG. 1 is an exploded view of a probe and a probe sheath according to the prior art.
Figure 2:
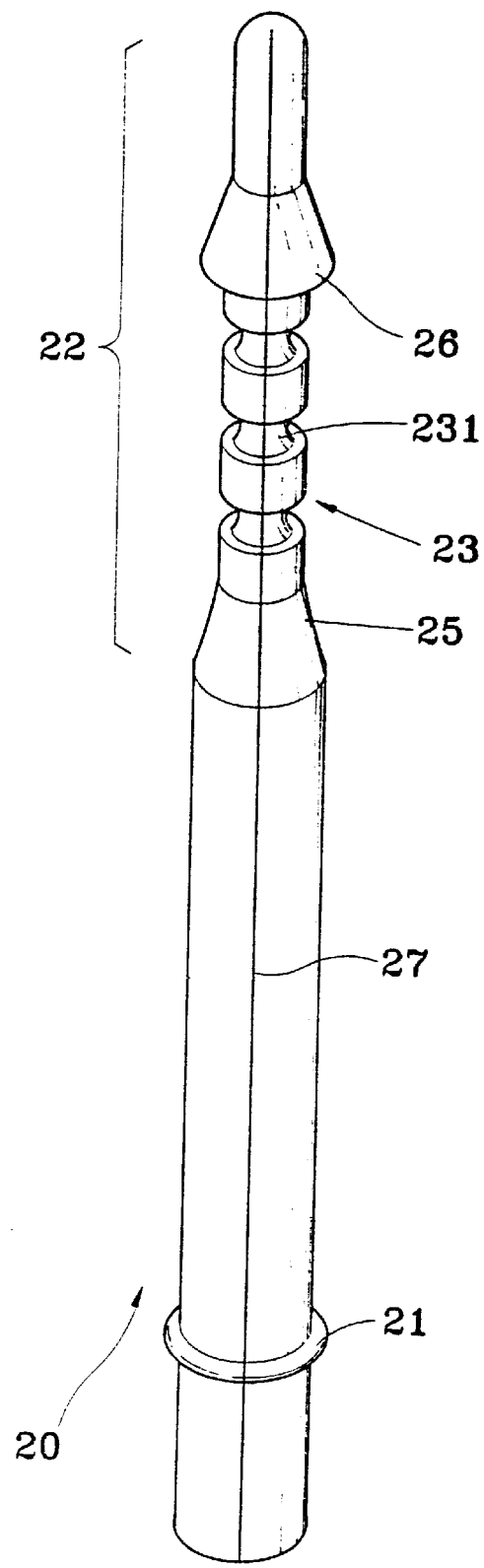
FIG. 2 is a perspective view of a probe sheath according to the present invention.
Figure 3:
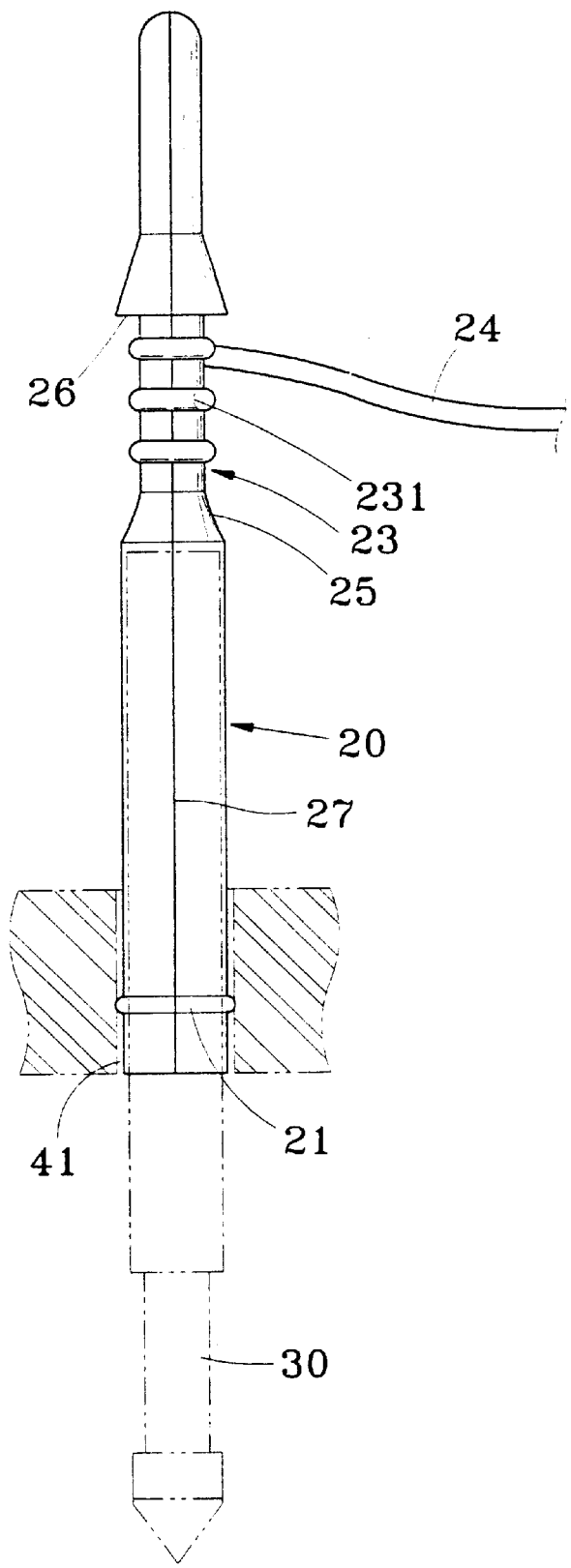
FIG. 3 is an installed view of the present invention.

Referring to FIGS. 2 and 3, a probe sheath 20 is provided to hold a probe 30. The probe sheath 20 is a tubular member having a flange 21 raised around the periphery of the tubular body thereof near one end, and an end piece 22 longitudinally extended from the tubular body at an opposite end. The end piece 22 comprises a neck 23, and two stop portions 25;26 at two opposite ends of the neck 23. One stop portion 26 has a conical profile with a flat bottom side facing the neck 23. A plurality of annular grooves 231 are made around the neck 23, and spaced between the stop portions 25;26. A lead wire 24 is provided having one end fastened to the annular grooves 231 around the neck 23.

Referring to FIG. 3 again, the probe sheath 20 is plugged into a plug hole 41 on a circuit board implement 40 to force the flange 21 into tight engagement with the plug hole 41. After installation of the probe sheath 20 in the plug hole 41, the probe 30 is inserted into the probe sheath 20.

Figure 4:
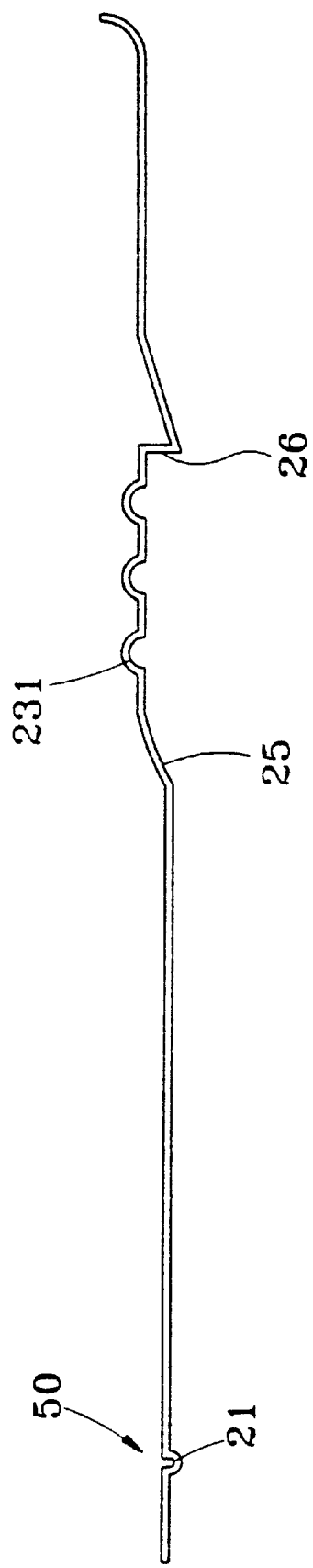
FIG. 4 is a side view of a metal sheet stamped into shape according to the present invention.

Referring to FIG. 4 and FIG. 2 again, a probe sheath 20 is made from a metal (copper) sheet 50 by stamping. When the metal (copper) sheet 50 is stamped into shape, it is cut into pieces, enabling each individual piece to be rolled up into a tubular member to form a respective probe sheath 20. When a probe sheath 20 is finished, a longitudinal split 27 is formed at the finished probe sheath 20. Because the bare conductor of one end of the lead wire 24 is fastened to the annular grooves 231 around the neck 23 between the stop portions 25;26, the lead wire 24 is firmly and electrically maintained connected to the probe sheath 20.

While only one embodiment of the present invention has been shown and described, it will be understood that various modifications and changes could be made thereunto without departing from the spirit and scope of the invention disclosed.

What I claimed is:

1. A metal probe sheath comprising a tubular body and an endpiece at one end of the tubular body, said endpiece comprising a neck to which a bare conductor of a lead wire is connected, and at least one stop portion at at least one end of said neck to stop said lead wire in place, wherein said at least one stop portion includes a conical stop portion at one end of said neck remote from said tubular body, said conical stop portion having a flat bottom side facing said neck.

2. The metal probe sheath of claim 1, wherein said neck comprises a plurality of annular grooves to which the bare conductor of said lead wire is fastened.

3. The metal probe sheath of claim 1, wherein said at least one stop portion includes a first stop portion and a second stop portion at two opposite ends of said neck.

4. The metal probe sheath of claim 1, which is made by stamping a metal sheet into shape and then rolling up the stamped metal sheet into a tubular member.

* * * * *